United States Patent
Sharma et al.

(10) Patent No.: US 9,141,763 B2
(45) Date of Patent: Sep. 22, 2015

(54) METHOD AND SYSTEM FOR PATIENT-SPECIFIC COMPUTATIONAL MODELING AND SIMULATION FOR COUPLED HEMODYNAMIC ANALYSIS OF CEREBRAL VESSELS

(75) Inventors: Puneet Sharma, Rahway, NJ (US); Tommaso Mansi, Westfield, NJ (US); Viorel Mihalef, Keasbey, NJ (US); Jingdan Zhang, Plainsboro, NJ (US); David Liu, Princeton, NJ (US); Shaohua Kevin Zhou, Plainsboro, NJ (US); Bogdan Georgescu, Plainsboro, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 817 days.

(21) Appl. No.: 13/366,677

(22) Filed: Feb. 6, 2012

(65) Prior Publication Data
US 2012/0203530 A1    Aug. 9, 2012

Related U.S. Application Data

(60) Provisional application No. 61/439,955, filed on Feb. 7, 2011.

(51) Int. Cl.
G06G 7/48    (2006.01)
G06G 7/50    (2006.01)
G06F 19/00    (2011.01)

(52) U.S. Cl.
CPC ................................. G06F 19/3437 (2013.01)

(58) Field of Classification Search
CPC .................................................. G06F 19/3437
USPC ..................................... 703/6, 9, 11; 600/507
See application file for complete search history.

(56) References Cited

U.S. PATENT DOCUMENTS

| 2008/0249755 | A1 | 10/2008 | Tek et al. | |
|---|---|---|---|---|
| 2009/0244061 | A1* | 10/2009 | De Putter et al. | 345/420 |
| 2010/0002925 | A1* | 1/2010 | Kiraly et al. | 382/131 |
| 2010/0298719 | A1* | 11/2010 | Kock et al. | 600/485 |
| 2011/0060576 | A1 | 3/2011 | Sharma et al. | |
| 2012/0022843 | A1 | 1/2012 | Ionasec et al. | |

OTHER PUBLICATIONS

Oshima et al. "Finite element simulation of blood flow in the cerebral artery". Elsevier, 2001. p. 661-671.*

(Continued)

*Primary Examiner* — Eunhee Kim

(57) ABSTRACT

A method and system for patient-specific computational modeling and simulation for coupled hemodynamic analysis of cerebral vessels is disclosed. An anatomical model of a cerebral vessel is extracted from 3D medical image data. The anatomical model of the cerebral vessel includes an inner wall and an outer wall of the cerebral vessel. Blood flow in the cerebral vessel and deformation of the cerebral vessel wall are simulated using coupled computational fluid dynamics (CFD) and computational solid mechanics (CSM) simulations based on the anatomical model of the cerebral vessel.

29 Claims, 7 Drawing Sheets

(56) References Cited

OTHER PUBLICATIONS

Deschamps et al. "Vessel Segmentation and blood flow simulation using Level-Sets and Embedded Boundary method". Elsevier, 2004. p. 75-80.*

L. Grady, "Random Walks for Image Segmentation", IEEE Transactions on Pattern Analysis and Machine Learning, pp. 1768-1783, vol. 28, No. 11.

* cited by examiner

METHOD AND SYSTEM FOR PATIENT-SPECIFIC COMPUTATIONAL MODELING AND SIMULATION FOR COUPLED HEMODYNAMIC ANALYSIS OF CEREBRAL VESSELS

This application claims the benefit of U.S. Provisional Application No. 61/439,955, filed Feb. 7, 2011, the disclosure of which is herein incorporated by reference.

BACKGROUND OF THE INVENTION

The present invention relates to hemodynamic analysis of cerebral vessels, and more particularly, to hemodynamic analysis of cerebral vessels using non-invasive patient-specific computational modeling and simulation based on medical image data.

In recent years, various techniques have been proposed for hemodynamic analysis using Computational Fluid Dynamics (CFD) and Computational Solid Mechanics (CSM). For example, such hemodynamic analysis has been proposed for various applications, such as determining the risk of rupture of aneurysms, assessment of stenosis severity, and assessment of atherosclerosis plaque formation. These techniques have also been proposed for simulating the hemodynamic effect of implanting a flow-diverter or stent for treating aneurysms or stenosis, as well as for determining hemodynamic attributes for preoperative planning and decision support.

Despite recent advances, computational mechanics based techniques are currently not used in routine clinical practice. One possible reason that computational mechanics based techniques are not prevalent is that such techniques are typically either based on simplified anatomical models or on population wide assumptions for certain model parameters, thereby rendering them unsuitable for analysis and decision support on an individual patient basis.

BRIEF SUMMARY OF THE INVENTION

The present invention provides a method and system for non-invasive patient-specific computational modeling and simulation for coupled hemodynamic analysis of cerebral vessels. The present inventors have determined that there is a lack of accurate anatomical models which contain information on cerebral vessel wall thickness. For the comprehensive patient-specific modeling and simulation provided by embodiments of the present invention, the estimation of accurate vessel geometry, including vessel wall thickness, is important, since the wall biomechanical parameters are highly dependent on an accurate model of the vessel wall. Due to the coupled nature of the solid-fluid modeling used in embodiments of the present invention, the underlying biomechanical calculations for the vessel wall directly affect the computational fluid dynamics (CFD) calculations for the blood flow in the cerebral vessels.

In one embodiment of the present invention, an anatomical model of a cerebral vessel is extracted from 3D medical image data. The anatomical model of the cerebral vessel includes an inner wall and an outer wall of the cerebral vessel. Blood flow in the cerebral vessel and deformation of the cerebral vessel wall are simulated using coupled computational fluid dynamics (CFD) and computational solid mechanics (CSM) simulations based on the anatomical model of the cerebral vessel.

These and other advantages of the invention will be apparent to those of ordinary skill in the art by reference to the following detailed description and the accompanying drawings.

DETAILED DESCRIPTION

Figure 1:
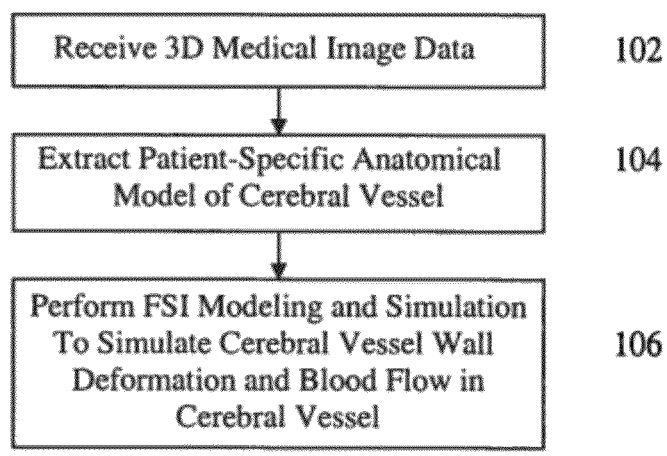
FIG. 1 illustrates a method for hemodynamic analysis of cerebral vessels according to an embodiment of the present invention.

The present invention relates to computational modeling and simulation for patient-specific coupled hemodynamic analysis in cerebral using patient-specific modeling of the cerebral vessels from sequences of volumetric medical image data, such as computed tomography (CT), rotational angiography, magnetic resonance imaging (MRI), and ultrasound data. In such sequences of volumetric data, also referred to herein as 4D image data or 4D images, each frame is a 3D image (volume). Embodiments of the present invention are described herein to give a visual understanding of the methods for generating a patient-specific cerebral vessel model and for computational modeling and simulation. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a computational framework for performing patient-specific coupled hemodynamic analysis in cerebral vessels. The results of such analysis can be used for pre-operative planning, risk assessment, decision support, and for comparing multiple possible interventions or therapies. Embodiments of the present invention use an accurate anatomical model of a cerebral vessel that includes vessel wall thickness for performing coupled fluid dynamics and solid mechanics computations. In particular, a learning based method is used for extracting an accurate patient-specific wall thickness, followed by a coupled fluid dynamics and solid mechanics solver for simulating wall deformation and fluid flow inside the cerebral vessel.

Embodiments of the present invention provide the following components: a learning based image segmentation framework for extracting the patient specific anatomic model of the cerebral vessel wall, including the vessel wall thickness, from 3D medical image data; a fluid structure interaction solver, including a computational fluid dynamics (CFD) solver and a computational solid mechanics (CSM) solver, that numerically models and simulates the coupled deformation of the vessel wall and the blood flow inside the vessel of interest; and automated parameter estimation to estimate the biomechanical parameters of the cerebral vessel wall from dynamic medical images.

In addition to generating hemodynamic parameters for the decision support framework, the computational modeling and simulation methodology may also be used for non-invasive assessment of surgical procedures on individual patients, as well as analyzing the effect of surgery on important hemodynamic parameters. This is achieved by appropriately modifying the patient-specific structure model (to reflect the surgical changes), together with the patient-specific boundary conditions, and then simulating the blood flow in the simulated post-operative anatomy.

FIG. 1 illustrates a method for hemodynamic analysis of cerebral vessels according to an embodiment of the present invention. The method of FIG. 1 transforms image data representing a brain region of a patient into a patient-specific anatomical model of a cerebral vessel and uses computational simulation techniques to simulate blood vessel wall deformation and blood flow in the cerebral vessel based on the patient-specific cerebral vessel model.

Referring to FIG. 1, at step 102, 3D medical image data is received. In particular, at least one 3D medical image (volume) is received. In certain embodiments, a sequence of 3D medical images acquired over a certain time period may be received. The 3D medical image data may be image data acquired from any medical image modality, such as CT, Rotational Angiography, MRI, or Ultrasound. The 3D medical image data can be received directly from an image acquisition device, such as a CT scanner. It is also possible that previously stored image data be loaded, for example from a memory or storage of a computer system or some other computer readable storage medium.

At step 104, a patient-specific anatomical model of at least one cerebral vessel is extracted from the 3D medical image data. The patient-specific anatomical model is an accurate anatomical model of the vessel(s) of interest that includes a surface mesh together with the vessel wall thickness. This patient-specific anatomical model of the cerebral vessel can be used to create computational meshes for solid (vessel wall) and fluid (vessel interior) domains. The computational meshes can then be used to numerically solve the couple fluid dynamics and solid mechanics for determining the vessel wall deformation and the blood flow inside the vessel.

Figure 2:
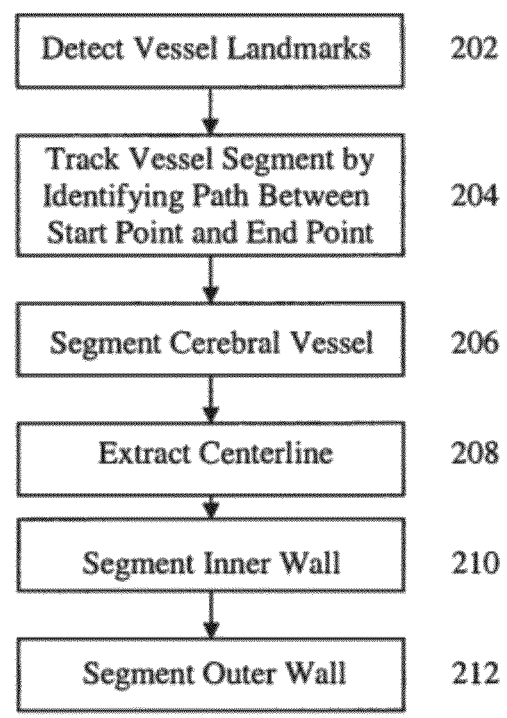
FIG. 2 illustrates a method for fully automatic cerebral vessel segmentation according to an embodiment of the present invention.

The anatomical modeling segments the inner and outer cerebral vessel walls in a given 3D image. FIG. 2 illustrates a method for fully automatic cerebral vessel segmentation according to an embodiment of the present invention. The method of FIG. 2 can be used to implement step 104 of FIG. 1. The method of FIG. 2 first localizes a segment of interest of a cerebral vessel, followed by centerline extraction, inner wall segmentation, and outer wall segmentation. Although the method of FIG. 2 is described as segmenting cerebral vessels, it is to be understood that the method may be similarly applied to segment coronary vessels in the heart or liver vessels in the liver.

As illustrated in FIG. 2, at step 202, vessel landmarks are detected in the 3D medical image. In order to localize the cerebral vessel, a trained landmark detector is used to identify a start point and an end point for the vessel. The landmark detector is trained using training data in which the ground truth position of each landmark (i.e., start point and end point) is annotated. This enables the learning system to generate a number of positive samples at the annotated ground truth positions, and a number of negative samples away from the ground truth positions. The positive and negative samples go through a feature extraction stage, where Haar features and steerable features are calculated for each sample. The features extracted fro the positive and negative samples are then fed to a statistical classifier, such as a Probabilistic Boosting Tree (PBT), which automatically learns to optimally separate positive and negative samples. The trained classifier evaluates voxels of the received 3D medical image and determines the probability that each voxel is a positive sample (i.e., start point or end point).

At step 204, the vessel segment is tracked by identifying a path between the start point and end point of the vessel segment. The landmark detection of step 202 results in the identification of the start point and the end point for a vessel segment. A shortest path algorithm based on the well-known Dijkstra's algorithm can then be used to identify a path between the start point and the end point. The shortest path algorithm specifies the cost between traveling across adjacent voxels. In a possible implementation, this cost is inversely proportional to the change in intensity. It is also possible to incorporate other factors, such as the gradient field (the path is discouraged from traveling through high gradients) and a spatial prior map based on the position relative to the start and end points (the path is encouraged to stay close to a certain path established by the spatial prior) as additional cost factors. The "shortest" path between the start point and the end point is identified by determining a path between the start point and end point with the lowest cost.

Figure 3:
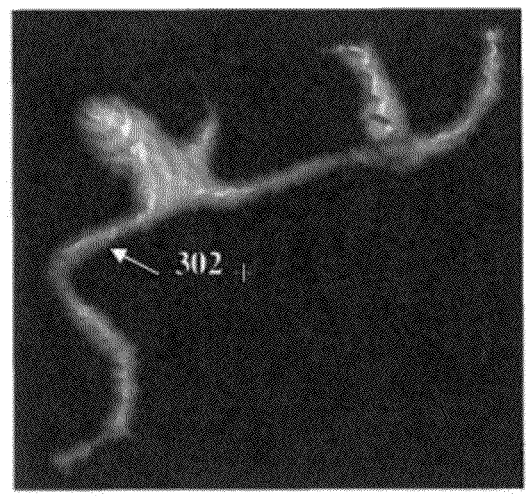
FIG. 3 illustrates exemplary segmentation results 302 of a cerebral vessel using the random walks algorithm.

At step 206, the vessel is segmented based on the tracked path between the start point and the end point. The shortest path between the start point and end point identified in step 204 is not necessarily the vessel centerline. In order to determine a more accurate centerline, the vessel is segmented in the 3D image. According to an advantageous implementation, the vessel segmentation can be obtained using a random walks algorithm based on the image intensities and gradients along the tracked path. The random walks algorithm is described in additional detail in L. Grady, "Random Walks for Image Segmentation", *IEEE Transactions on Pattern Analysis and Machine Learning*, pp. 1768-1783, Vol. 28, No. 11, which is incorporated herein by reference. FIG. 3 illustrates exemplary segmentation results 302 of a cerebral vessel using the random walks algorithm.

Returning to FIG. 2, at step 208, a vessel centerline is extracted from the segmented cerebral vessel. The centerline can be extracted using any centerline extraction method. For example, the centerline of the segmented cerebral vessel can be extracted using the centerline extraction technique described in United States Published Patent Application No. 2008/0249755, which is incorporated herein by reference.

At step 210, the inner vessel wall of the vessel segment is segmented. The vessel segmentation of step 206 used for the centerline extraction provides a rough segmentation of the vessel, but is not accurate enough to differentiate inner and outer walls of the vessel. Accordingly, embodiments of the present invention utilize a learning based approach to accurately segment the inner and outer walls by leveraging boundary classifiers learned from annotated training data.

Figure 4:
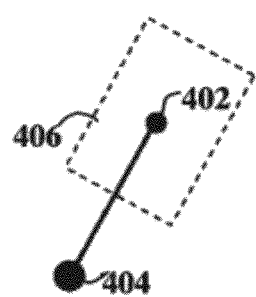
FIG. 4 illustrates determining a local orientation for a voxel hypothesis.

After centerline extraction, cross sections of the 3D image are extracted along the centerline, and a warped volume is generated by assembling the 2D cross section images. In order to segment the inner vessel wall, a probability is determined for each voxel in the warped volume, of that voxel of being on the boundary of the inner wall. The probability for each voxel is determined using a trained boundary classifier. For example, the trained boundary classifier may be trained using a PBT based on annotated training data. For each boundary voxel hypothesis in the warped volume, a local orientation is calculated by connecting the voxel hypothesis to the vessel center in the same 2D cross section. Based on the local orientation, steerable features are calculated in a neighborhood around the voxel hypothesis, and the steerable features are used by the trained boundary classifier to calculate the probability score for that hypothesis voxel. FIG. 4 illustrates determining a local orientation for a voxel hypothesis. As shown in FIG. 4, the local orientation for voxel 402 is determined by connecting voxel 402 to the vessel center point 404 in the 2D cross section. A neighborhood 406 is that is aligned to the local orientation is then defined around voxel 402 and steerable features are calculated within the neighborhood.

In offline training of the boundary classifier, voxels close to the ground truth inner wall annotation are used as positive samples and the remaining voxels are used as negative samples. In online segmentation, the boundary classifier scans all voxels in the warped volume and calculates a probability volume map (i.e., a probability score for each pixel). Then, the random walks algorithm is applied to segment the inner vessel wall based on the probability map calculated by the trained boundary classifier.

Figure 5:
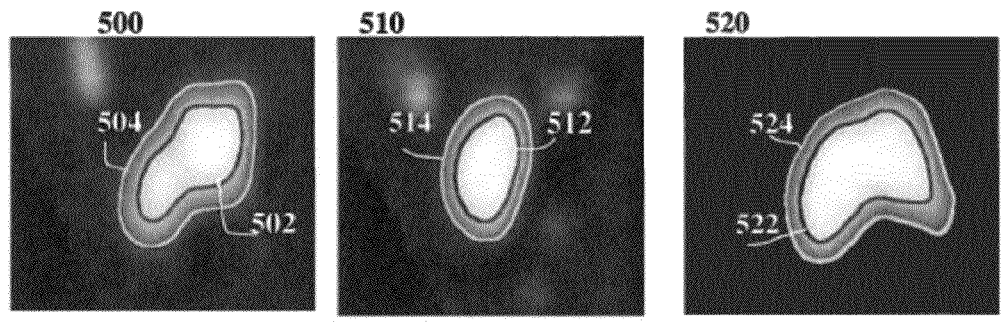
FIG. 5 illustrates exemplary inner wall and outer wall segmentation results.

At step 212, the outer vessel wall of the vessel segment is segmented. After the inner vessel wall is segmented, a similar learning approach is applied to segment the outer vessel wall using a trained boundary detector. In segmenting the outer wall, prior knowledge that the outer wall must be outside of the inner wall is enforced by assigning voxels within the segmented inner wall to have a probability score of zero in the probability map calculated for the outer wall. The random walks algorithm is then applied to segment the outer wall based on the probability map. FIG. 5 illustrates exemplary inner wall and outer wall segmentation results. As shown in FIG. 5, images 500, 510, and 520 show cross sections along the centerline of a cerebral vessel. Segmentation results for the inner wall 502, 512, and 522 and the outer wall 504, 514, and 524 of the vessel are shown in images 500, 510, and 520, respectively. It is clear that the segmentation of the inner wall and the outer wall of a vessel results in an anatomical model of the vessel that includes the vessel thickness.

Returning to FIG. 1, at step 106, fluid structure interaction (FSI) modeling and simulation is performed using the anatomical model of the cerebral vessel to iteratively solve for wall deformation of the cerebral vessel wall and the blood flow within the cerebral vessel. The FSI uses coupled computational solid mechanics (CSM) and computational fluid dynamics (CFD) to simulate the deformation of the vessel wall due to the flow in the vessel and to simulate the flow of the blood in the vessel due to the wall deformation and pressure gradients.

The FSI framework includes the following components: an FSI pre-processor, a CFD solver, a CSM solver, a coupling interface, a parameter estimation module, and a post-processor. These components can be implemented on one or more computers, for example, by a processor executing computer executable instructions defining operations of the components.

The FSI pre-processor generates computational meshes from the cerebral vessel anatomical model extracted from the medical image data. The FSI pre-processor reads the inner wall surface mesh generated from the image data and generates a computational mesh for the CFD solver from the inner wall surface mesh. The FSI pre-processor also specifies the boundary conditions and initial conditions on the CFD computational mesh and specifies the properties of the blood. The boundary conditions for the CFD computational mesh may include an inlet boundary condition and an outflow boundary condition. The inlet boundary condition is the velocity value or flow rate value at the inlet of the vessel, and can be assigned an idealized value or can be determined as a patient-specific value using Doppler measurements. The outflow boundary condition can be a pressure-based on flow-based boundary condition at the outlet of the vessel. The FSI pre-processor specifies the initial boundary condition at a time step t=0. The blood density and dynamic viscosity can be set to generic mean values across healthy individuals, namely $\rho=1.05$ g/cm$^3$ and $\mu=4$ mPa·s.

The FSI pre-processor also reads the anatomical cerebral vessel wall model (including the inner wall and the outer wall) and generates a computational mesh for the CSM solver from the inner wall surface mesh and outer wall surface mesh. The FSI pre-processor imposes the boundary conditions and initial conditions on the CSM computational mesh and specifies the mechanical properties of the vessel wall. The initial boundary conditions can be imposed using the inner and outer wall positions in the patient-specific anatomical model, and the mechanical properties of the vessel wall can be specified using expected values based on population wide data.

Figure 6:
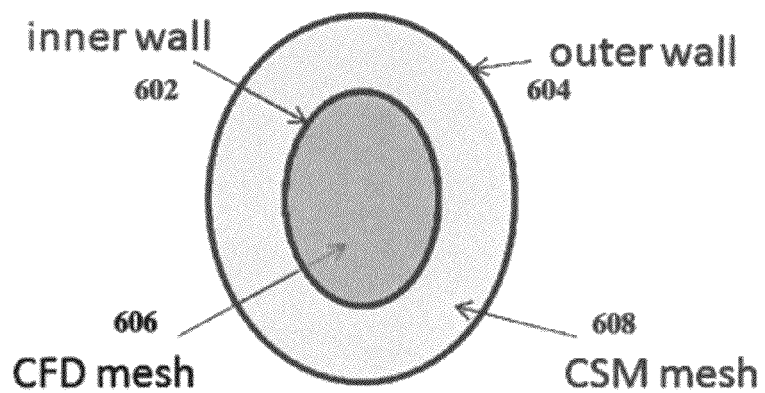
FIG. 6 illustrates the creation of the CFD computational mesh and the CSM computational mesh from a patient-specific anatomical model of a cerebral vessel.

FIG. 6 illustrates the creation of the CFD computational mesh and the CSM computational mesh from a patient-specific anatomical model of a cerebral vessel. As illustrated in FIG. 6, a cross section of the anatomical model of the cerebral vessel shows the inner wall 602 and the outer wall 604. The CFD mesh 606 represents the interior of the vessel and is created within the inner vessel wall 602. The CSM mesh 608 represents the vessel wall itself and is created between the inner vessel wall 602 and the out vessel wall 604.

The CFD solver derives realistic hemodynamics, by numerically solving a set of partial differential equations (PDEs), such as Navier-Stokes equations, that describe the blood flow in the cerebral vessel. The PDEs are numerically solved by discretizing them both spatially and temporally, and iteratively solving for the velocities and pressure. The solution is progressed from one time-point to the next by a time-stepping scheme that can be implicit or explicit. The patient specific geometry serves as an input to the CFD solver and the solution to the PDEs is constrained by the local anatomy of the cerebral vessel.

The CSM solver is a Finite Element Method (FEM) based solver that reads the vessel wall mesh that contains the outer surface mesh and the inner surface mesh, and numerically solves the solid mechanics equations that describe the displacement of the mesh nodes under a mechanical loading. The mechanical properties of the vessel wall can be pre-specified, for example as an average of population wide data, or can be estimated based on the patient-specific medical image data.

Figure 7:
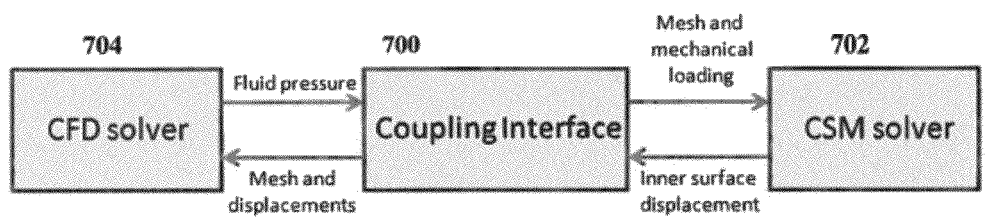
FIG. 7 illustrates the coupling interface interacting with the CFD solver and the CSM solver.

The coupling interface is an interface between the CFD solver and the CSM solver in order to provide coupled hemodynamic analysis in which simulated outputs of each time step in the CFD solver affect the simulated wall deformation in the CSM solver and outputs of each time step in the CSM solver affect the blood flow simulation in the CFD solver. FIG. 7 illustrates the coupling interface interacting with the CFD solver and the CSM solver. As shown in FIG. 7, the coupling interface 700 provides the vessel wall mesh (CSM computational mesh) and the mechanical loading (due to fluid pressure estimate by the CFD solver) to the CSM solver 702, and the fluid mesh (CFD computational mesh) and the inner-wall displacements to the CFD solver 704. The coupling interface receives the fluid pressure on the interface nodes (nodes on the inner wall, i.e., the interface between the CSM computational mesh and the CFD computational mesh) from the CFD solver 704 and the displacement of these nodes from the CSM solver 702. The exchange of information is carried out a specific time points during the simulations, which is governed by the coupling interface. In the interim of these information exchange points, both the CFD solver and the CSM solver iterate their solutions using their internal time stepping schemes.

The parameter estimation module is used to estimate the mechanical properties of the cerebral vessel wall. The parameter estimation is performed by coupling the FSI framework with inverse problem strategies (e.g., Kalman filtering or trust region techniques). This includes adjusting the model parameters used to model the cerebral vessel wall such that the wall motion simulated by the CSM solver matches the observed motion in a sequence of medical images. This is done in an optimization framework, where the goal is to minimize a cost function that evaluates the difference between the simulated vessel wall motion and the motion extracted from the medical images.

The post-processor receives the results from the CFD and CSM solvers, in addition to the medical image data and surface meshes, and calculates derived hemodynamic quantities, such as wall shear stress, vorticity, oscillatory shear index, energy loss, etc.) from the FSI results. The post-processor can store the derived hemodynamic quantities in a database. Additionally, the post-processor also extracts features from the flow data, such as vortex cores, flow separation, etc., and stored the extracted features in a database.

Figure 8:
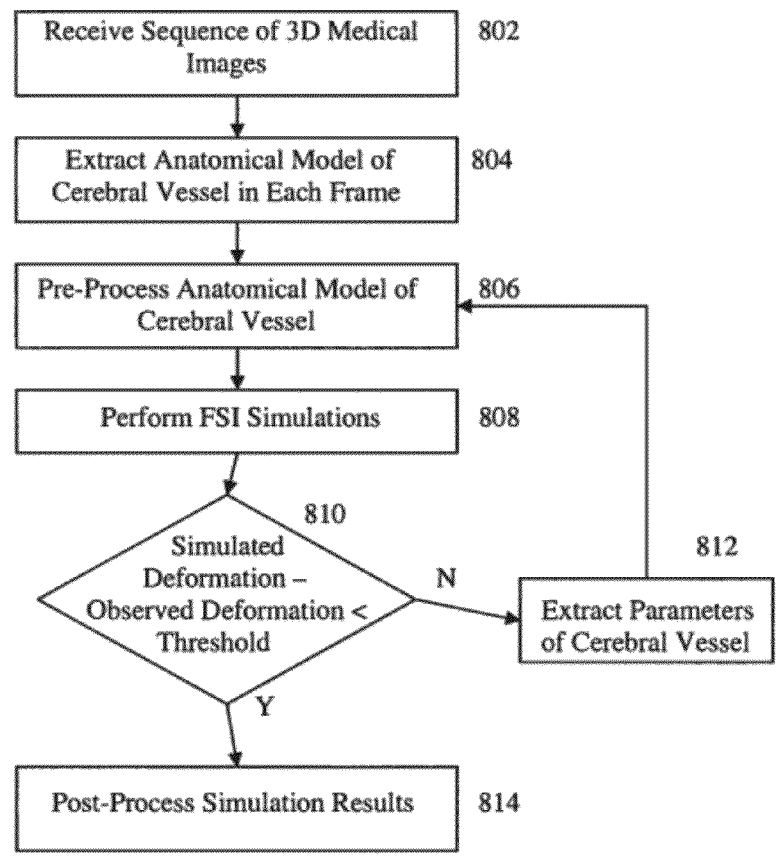
FIG. 8 illustrates a method for FSI modeling and simulation using cerebral wall parameter estimation according to an embodiment of the present invention.

FIG. 8 illustrates a method for FSI modeling and simulation using cerebral wall parameter estimation according to an embodiment of the present invention. As illustrated in FIG. 8, at step 802, a sequence of 3D medical image data is received. At step 804, a patient-specific anatomical model of a cerebral vessel is extracted in each frame of the sequence of 3D medical image data. It is to be understood that the method of FIG. 2, described above, can be used to extract the patient-specific anatomical model in each frame.

At step 806, the FSI pre-processor generates the computational meshes, sets the initial boundary conditions for the FSI simulations, and sets the mechanical parameters of the cerebral vessel wall. The mechanical parameters can be initialized using population wide data. In each subsequent iteration of the method, the parameters are set as the parameters estimated in the parameter estimation step 812.

At step 808, FSI simulation is performed by performing coupled CFD and CSM simulations. As described above, the CFD solver simulated blood flow in the cerebral vessel, the CSM solver simulated the deformation of the cerebral vessel wall, and the coupling interface exchanges information between the CFD solver and the CSM solver. In particular, the CFD solver generates pressure and velocity values for the blood flow over a number of time steps based at least in part on deformations of the inner wall of the cerebral vessel. The coupling interface receives the fluid pressure values calculated by the CFD solver, calculates a corresponding mechanical loading onto mesh points of the inner vessel wall, and provides the mechanical loading to the CSM solver. The CSM solver simulates the deformations of the cerebral vessel wall based at least in part on the mechanical loading on the inner vessel wall due to the fluid pressure. The coupling interface received the simulated displacements of the inner vessel wall and provides these displacements to the CFD solver.

At step 810, it is determined if the difference (residue) between the simulated cerebral wall deformation by the CSM solver and the observed cerebral wall deformation in the sequence of 3D medical images is less than a threshold value. If the difference between the simulated and observed deformation of the cerebral wall is not less than the threshold value, the method proceeds to step 812. If the difference between the simulated deformation and the observed deformation is less than the threshold value, the method proceeds to step 814.

At step 812, mechanical parameters of the cerebral vessel wall are estimated. The parameters can be parameters of a model that characterizes the mechanical properties of the cerebral vessel wall. These parameters can be estimated using inverse problem strategies to reduce the difference between the simulated deformation and the observed deformation. Once new parameters are determined, the method returns to step 806. Steps 806-812 are then repeated until the difference between the simulated deformation and the observed deformation is below the threshold. It is to be understood that the final time that the FSI simulation (step 808) is performed, the FSI simulation will be performed with accurate patient-specific mechanical properties for the cerebral vessel wall, and will generate the final FSI simulation results.

At step 814, the FSI simulation results are post-processed to derive hemodynamic quantities, such as wall shear stress, vorticity, oscillatory shear index, energy loss, etc., and to extract features from the flow data, such as vortex cores, flow separation, etc.

Figure 9:
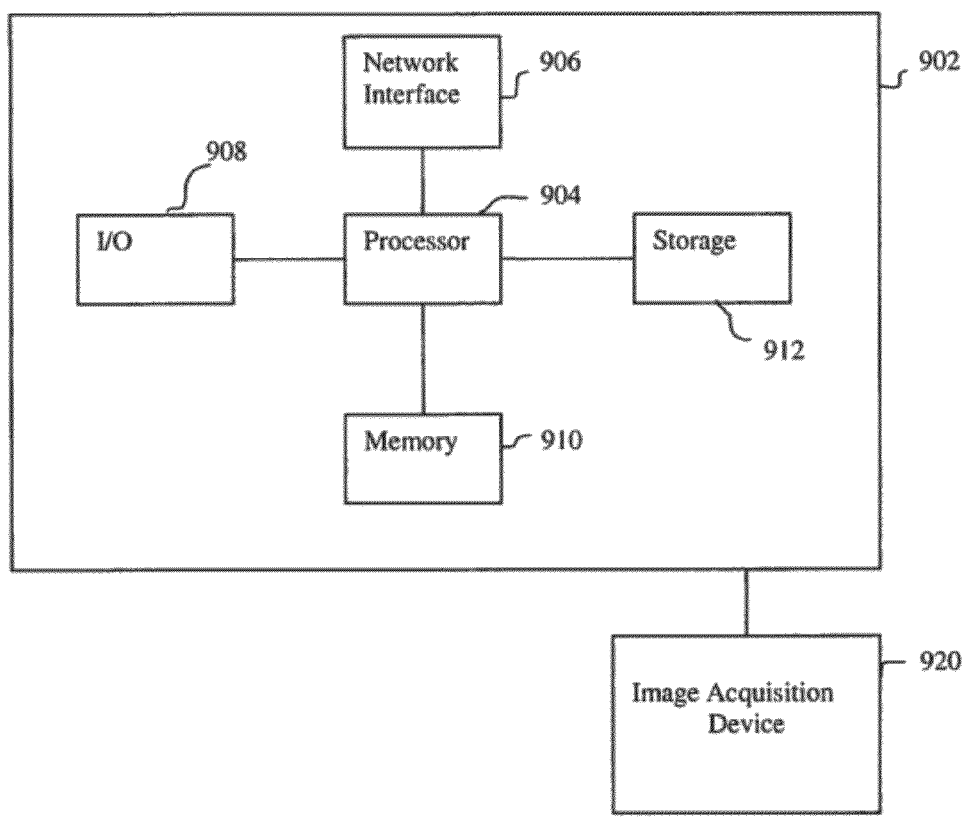
FIG. 9 is a high-level block diagram of a computer capable of implementing the present invention.

The above-described methods for computational modeling and simulation for coupled hemodynamic analysis of cerebral vessels may be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 1, 2, and 8 may be defined by the computer program instructions stored in the memory 910 and/or storage 912 and controlled by the processor 904 executing the computer program instructions. An image acquisition device 920, such as a CT scanning device, can be connected to the computer 902 to input image data to the computer 902. It is possible to implement the image acquisition device 920 and the computer 902 as one device. It is also possible that the image acquisition device 920 and the computer 902 communicate wirelessly through a network. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for hemodynamic analysis of cerebral vessels, comprising:
   extracting an anatomical model of a cerebral vessel from 3D medical image data, the anatomical model of the cerebral vessel including an inner wall and an outer wall of the cerebral vessel; and
   simulating blood flow in the cerebral vessel and deformation of the cerebral vessel wall using coupled computational fluid dynamics (CFD) and computational solid mechanics (CSM) simulations based on the anatomical model of the cerebral vessel.

2. The method of claim 1, wherein the step of extracting an anatomical model of a cerebral vessel from 3D medical image data comprises:
   detecting a start point and an end point of a vessel segment in the 3D medical image data;
   extracting a centerline of the cerebral vessel between the start point and the end point;
   generating a warped volume by assembling 2D cross section images extracted along the centerline;
   segmenting an inner wall of the cerebral vessel in the warped volume using a trained inner boundary classifier; and
   segmenting an outer wall of the cerebral vessel in the warped volume using a trained outer boundary classifier.

3. The method of claim 2, wherein the step of extracting a centerline of the cerebral vessel between the start point and the end point comprises:
   identifying a path between the start point and the end point;
   segmenting the cerebral vessel using a random walks algorithm based on image intensities and gradients along the path; and
   extracting the centerline of the segmented cerebral vessel.

4. The method of claim 2, wherein the step of segmenting an inner wall of the cerebral vessel in the warped volume using a trained inner boundary classifier comprises:
   generating a first probability map by calculating a probability value for each of a plurality of voxels in the warped volume using the trained inner boundary classifier; and
   segmenting the inner wall of the cerebral vessel using a random walks algorithm based on the first probability map.

5. The method of claim 4, wherein the step of segmenting an outer wall of the cerebral vessel in the warped volume using a trained outer boundary classifier comprises:
   generating a second probability map by calculating a probability value for each of a plurality of voxels in the warped image using the trained outer boundary detector, wherein voxels within the segmented inner wall of the cerebral vessel are assigned a probability value of zero; and
   segmenting the outer wall of the cerebral vessel using a random walks algorithm based on the second probability map.

6. The method of claim 2, wherein the step of segmenting an inner wall of the cerebral vessel in the warped volume using a trained inner boundary classifier comprises:
   determining an orientation for each of a plurality of voxels in the warped volume by connecting each voxel to a vessel center point in the same 2D cross section;
   defining a neighborhood around each of the plurality of voxels, the neighborhood around each voxel aligned with the orientation determined for the voxel;
   extracting steerable features in the neighborhood defined around each voxel; and
   calculating a probability value for each voxel based on the steerable features extracted in the neighborhood defined around each voxel using the trained inner boundary classifier.

7. The method of claim 2, wherein the step of segmenting an outer wall of the cerebral vessel in the warped volume using a trained outer boundary classifier comprises:
   determining an orientation for each of a plurality of voxels in the warped volume by connecting each voxel to a vessel center point in the same 2D cross section;
   defining a neighborhood around each of the plurality of voxels, the neighborhood around each voxel aligned with the orientation determined for the voxel;
   extracting steerable features in the neighborhood defined around each voxel; and
   calculating a probability value for each voxel based on the steerable features extracted in the neighborhood defined around each voxel using the trained outer boundary classifier.

8. The method of claim 1, wherein the step of simulating blood flow in the cerebral vessel and deformation of the cerebral vessel wall using coupled computational fluid dynamics (CFD) and computational solid mechanics (CSM) simulations based on the anatomical model of the cerebral vessel comprises:
   pre-processing the anatomical model of the cerebral vessel to generate a computational CFD mesh and a computational CSM mesh;
   performing CFD simulation on the CFD mesh by numerically solving partial differential equations to calculate simulated velocity and pressure of the blood flow in the cerebral vessel wall based on simulated deformations of the cerebral vessel wall; and
   performing CSM simulation on the CSM mesh by numerically solving solid mechanics equations to calculate the simulated deformations of cerebral vessel wall based on mechanical loading due to the simulate pressure of the blood flow in the cerebral vessel.

9. The method of claim 8, wherein the step of pre-processing the anatomical model of the cerebral vessel to generate a computational CFD mesh and a computational CSM mesh comprises:
   generating the CFD mesh within the inner wall of the anatomical model of the cerebral vessel; and
   generating the CSM mesh between the inner wall and the outer wall of the anatomical model of the cerebral vessel.

10. The method of claim 1, further comprising:
    estimating mechanical properties of the cerebral vessel wall to minimize a cost function that evaluates a difference between the simulated deformation of the cerebral vessel wall and an observed deformation in the anatomical model of the cerebral vessel wall extracted from the medical image data.

11. The method of claim 10, further comprising:
    repeating the step of simulating blood flow in the cerebral vessel and deformation of the cerebral vessel wall using coupled computational fluid dynamics (CFD) and computational solid mechanics (CSM) simulations based on the anatomical model of the cerebral vessel using the estimated mechanical properties of the cerebral vessel wall.

12. An apparatus for hemodynamic analysis of cerebral vessels, comprising:
 means for extracting an anatomical model of a cerebral vessel from 3D medical image data, the anatomical model of the cerebral vessel including an inner wall and an outer wall of the cerebral vessel; and
 means for simulating blood flow in the cerebral vessel and deformation of the cerebral vessel wall using coupled computational fluid dynamics (CFD) and computational solid mechanics (CSM) simulations based on the anatomical model of the cerebral vessel.

13. The apparatus of claim 12, wherein the means for extracting an anatomical model of a cerebral vessel from 3D medical image data comprises:
 means for detecting a start point and an end point of a vessel segment in the 3D medical image data;
 means for extracting a centerline of the cerebral vessel between the start point and the end point;
 means for generating a warped volume by assembling 2D cross section images extracted along the centerline;
 means for segmenting an inner wall of the cerebral vessel in the warped volume using a trained inner boundary classifier; and
 means for segmenting an outer wall of the cerebral vessel in the warped volume using a trained outer boundary classifier.

14. The apparatus of claim 13, wherein the means for segmenting an inner wall of the cerebral vessel in the warped volume using a trained inner boundary classifier comprises:
 means for generating a first probability map by calculating a probability value for each of a plurality of voxels in the warped volume using the trained inner boundary classifier; and
 means for segmenting the inner wall of the cerebral vessel using a random walks algorithm based on the first probability map.

15. The apparatus of claim 14, wherein the means for segmenting an outer wall of the cerebral vessel in the warped volume using a trained outer boundary classifier comprises:
 means for generating a second probability map by calculating a probability value for each of a plurality of voxels in the warped image using the trained outer boundary detector, wherein voxels within the segmented inner wall of the cerebral vessel are assigned a probability value of zero; and
 means for segmenting the outer wall of the cerebral vessel using a random walks algorithm based on the second probability map.

16. The apparatus of claim 13, wherein the means for segmenting an inner wall of the cerebral vessel in the warped volume using a trained inner boundary classifier comprises:
 means for determining an orientation for each of a plurality of voxels in the warped volume by connecting each voxel to a vessel center point in the same 2D cross section;
 means for defining a neighborhood around each of the plurality of voxels, the neighborhood around each voxel aligned with the orientation determined for the voxel;
 means for extracting steerable features in the neighborhood defined around each voxel; and
 means for calculating a probability value for each voxel based on the steerable features extracted in the neighborhood defined around each voxel using the trained inner boundary classifier.

17. The apparatus of claim 13, wherein the means for segmenting an outer wall of the cerebral vessel in the warped volume using a trained outer boundary classifier comprises:
 means for determining an orientation for each of a plurality of voxels in the warped volume by connecting each voxel to a vessel center point in the same 2D cross section;
 means for defining a neighborhood around each of the plurality of voxels, the neighborhood around each voxel aligned with the orientation determined for the voxel;
 means for extracting steerable features in the neighborhood defined around each voxel; and
 means for calculating a probability value for each voxel based on the steerable features extracted in the neighborhood defined around each voxel using the trained outer boundary classifier.

18. The apparatus of claim 12, wherein the means for simulating blood flow in the cerebral vessel and deformation of the cerebral vessel wall using coupled computational fluid dynamics (CFD) and computational solid mechanics (CSM) simulations based on the anatomical model of the cerebral vessel comprises:
 means for pre-processing the anatomical model of the cerebral vessel to generate a computational CFD mesh and a computational CSM mesh;
 means for performing CFD simulation on the CFD mesh by numerically solving partial differential equations to calculate simulated velocity and pressure of the blood flow in the cerebral vessel wall based on simulated deformations of the cerebral vessel wall; and
 means for performing CSM simulation on the CSM mesh by numerically solving solid mechanics equations to calculate the simulated deformations of cerebral vessel wall based on mechanical loading due to the simulate pressure of the blood flow in the cerebral vessel.

19. The apparatus of claim 12, further comprising:
 means for estimating mechanical properties of the cerebral vessel wall to minimize a cost function that evaluates a difference between the simulated deformation of the cerebral vessel wall and an observed deformation in the anatomical model of the cerebral vessel wall extracted from the medical image data.

20. A non-transitory computer readable medium encoded with computer executable instructions defining a method for hemodynamic analysis of cerebral vessels, the method:
 extracting an anatomical model of a cerebral vessel from 3D medical image data, the anatomical model of the cerebral vessel including an inner wall and an outer wall of the cerebral vessel; and
 simulating blood flow in the cerebral vessel and deformation of the cerebral vessel wall using coupled computational fluid dynamics (CFD) and computational solid mechanics (CSM) simulations based on the anatomical model of the cerebral vessel.

21. The non-transitory computer readable medium of claim 20, wherein the step of extracting an anatomical model of a cerebral vessel from 3D medical image data comprises:
 detecting a start point and an end point of a vessel segment in the 3D medical image data;
 extracting a centerline of the cerebral vessel between the start point and the end point;
 generating a warped volume by assembling 2D cross section images extracted along the centerline;
 segmenting an inner wall of the cerebral vessel in the warped volume using a trained inner boundary classifier; and
 segmenting an outer wall of the cerebral vessel in the warped volume using a trained outer boundary classifier.

22. The non-transitory computer readable medium of claim 21, wherein the step of segmenting an inner wall of the cerebral vessel in the warped volume using a trained inner boundary classifier comprises:
  generating a first probability map by calculating a probability value for each of a plurality of voxels in the warped volume using the trained inner boundary classifier; and
  segmenting the inner wall of the cerebral vessel using a random walks algorithm based on the first probability map.

23. The non-transitory computer readable medium of claim 22, wherein the step of segmenting an outer wall of the cerebral vessel in the warped volume using a trained outer boundary classifier comprises:
  generating a second probability map by calculating a probability value for each of a plurality of voxels in the warped image using the trained outer boundary detector, wherein voxels within the segmented inner wall of the cerebral vessel are assigned a probability value of zero; and
  segmenting the outer wall of the cerebral vessel using a random walks algorithm based on the second probability map.

24. The non-transitory computer readable medium of claim 21, wherein the step of segmenting an inner wall of the cerebral vessel in the warped volume using a trained inner boundary classifier comprises:
  determining an orientation for each of a plurality of voxels in the warped volume by connecting each voxel to a vessel center point in the same 2D cross section;
  defining a neighborhood around each of the plurality of voxels, the neighborhood around each voxel aligned with the orientation determined for the voxel;
  extracting steerable features in the neighborhood defined around each voxel; and
  calculating a probability value for each voxel based on the steerable features extracted in the neighborhood defined around each voxel using the trained inner boundary classifier.

25. The non-transitory computer readable medium of claim 21, wherein the step of segmenting an outer wall of the cerebral vessel in the warped volume using a trained outer boundary classifier comprises:
  determining an orientation for each of a plurality of voxels in the warped volume by connecting each voxel to a vessel center point in the same 2D cross section;
  defining a neighborhood around each of the plurality of voxels, the neighborhood around each voxel aligned with the orientation determined for the voxel;
  extracting steerable features in the neighborhood defined around each voxel; and
  calculating a probability value for each voxel based on the steerable features extracted in the neighborhood defined around each voxel using the trained outer boundary classifier.

26. The non-transitory computer readable medium of claim 20, wherein the step of simulating blood flow in the cerebral vessel and deformation of the cerebral vessel wall using coupled computational fluid dynamics (CFD) and computational solid mechanics (CSM) simulations based on the anatomical model of the cerebral vessel comprises:
  pre-processing the anatomical model of the cerebral vessel to generate a computational CFD mesh and a computational CSM mesh;
  performing CFD simulation on the CFD mesh by numerically solving partial differential equations to calculate simulated velocity and pressure of the blood flow in the cerebral vessel wall based on simulated deformations of the cerebral vessel wall; and
  performing CSM simulation on the CSM mesh by numerically solving solid mechanics equations to calculate the simulated deformations of cerebral vessel wall based on mechanical loading due to the simulate pressure of the blood flow in the cerebral vessel.

27. The non-transitory computer readable medium of claim 26, wherein the step of pre-processing the anatomical model of the cerebral vessel to generate a computational CFD mesh and a computational CSM mesh comprises:
  generating the CFD mesh within the inner wall of the anatomical model of the cerebral vessel; and
  generating the CSM mesh between the inner wall and the outer wall of the anatomical model of the cerebral vessel.

28. The non-transitory computer readable medium of claim 20, further comprising:
  estimating mechanical properties of the cerebral vessel wall to minimize a cost function that evaluates a difference between the simulated deformation of the cerebral vessel wall and an observed deformation in the anatomical model of the cerebral vessel wall extracted from the medical image data.

29. The non-transitory computer readable medium of claim 28, further comprising:
  repeating the step of simulating blood flow in the cerebral vessel and deformation of the cerebral vessel wall using coupled computational fluid dynamics (CFD) and computational solid mechanics (CSM) simulations based on the anatomical model of the cerebral vessel using the estimated mechanical properties of the cerebral vessel wall.

* * * * *